(12) United States Patent
Zdeblick et al.

(10) Patent No.: US 6,375,655 B1
(45) Date of Patent: *Apr. 23, 2002

(54) INTERBODY FUSION DEVICE AND METHOD FOR RESTORATION OF NORMAL SPINAL ANATOMY

(75) Inventors: Thomas Zdeblick, Madison, WI (US); Eddie Ray, III, Cordova; Lawrence M. Boyd, Memphis, both of TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/489,317

(22) Filed: Jan. 21, 2000

Related U.S. Application Data

(63) Continuation of application No. 09/209,602, filed on Dec. 11, 1998, now abandoned, which is a continuation of application No. 09/157,735, filed on Sep. 21, 1998, now abandoned, which is a continuation of application No. 09/111,197, filed on Jul. 7, 1998, now abandoned, which is a continuation of application No. 08/882,611, filed on Jun. 25, 1997, now abandoned, which is a continuation of application No. 08/835,306, filed on Apr. 7, 1999, now abandoned, which is a continuation of application No. 08/413,353, filed on Mar. 30, 1995, now Pat. No. 5,669,909, which is a continuation-in-part of application No. 08/411,017, filed on Mar. 27, 1995, now Pat. No. 5,782,919.

(51) Int. Cl.[7] .............................................. A61B 17/56

(52) U.S. Cl. .................... 606/61; 623/17.11; 623/17.16

(58) Field of Search .................... 606/61; 623/17.11, 623/17.16

(56) References Cited

U.S. PATENT DOCUMENTS

| | | | |
|---|---|---|---|
| 3,486,505 A | 12/1969 | Morrison | 128/303 |
| 3,848,601 A | 11/1974 | Ma et al. | 128/305 |
| 4,309,777 A | 1/1982 | Patil | 3/1.91 |

(List continued on next page.)

FOREIGN PATENT DOCUMENTS

| | | | |
|---|---|---|---|
| DE | 3505567 A | 6/1986 | A61F/2/28 |
| EP | 0077159 | 10/1982 | A61B/17/00 |
| EP | 0179695 | 9/1985 | A61F/2/44 |
| EP | 0635246 | 1/1995 | A61F/2/44 |
| EP | 0646366 | 5/1995 | |
| EP | 0637440 | 8/1995 | |
| FR | 2710519 A1 | 9/1993 | A61B/17/70 |
| WO | WO 87/07827 | 12/1987 | A61F/2/44 |

(List continued on next page.)

*Primary Examiner*—David O. Reip
*Assistant Examiner*—Julian W. Woo
(74) *Attorney, Agent, or Firm*—Woodward, Emhardt, Naughton, Moriarty & McNett

(57) ABSTRACT

An interbody fusion device in one embodiment includes a tapered body defining a hollow interior for receiving bone graft or bone substitute material. The body defines exterior threads which are interrupted over portions of the outer surface of the device. The fusion device defines truncated side walls so that on end view the body takes on a cylindrical form. The side walls are provided with vascularization openings, and the body wall device includes opposite bone ingrowth slots extending through the interrupted thread portion of the body. In another embodiment, the tapered body is solid and formed of a porous biocompatible material having sufficient structural integrity to maintain the intra-discal space and normal curvature. The material is preferably a porous tantalum having fully interconnected pores to facilitate complete bone tissue ingrowth into the implant. An implant driver is provided which engages the truncated side walls to complete the cylindrical form of the implant at the root diameter of the interrupted threads, to thereby facilitate threaded insertion of the implant to the intra-discal space between adjacent vertebrae. Methods for posterior and anterior insertion of the fusion device are also disclosed.

27 Claims, 11 Drawing Sheets

U.S. PATENT DOCUMENTS

| | | | |
|---|---|---|---|
| 4,349,921 A | 9/1982 | Kuntz | 3/1 |
| 4,501,269 A | 2/1985 | Bagby | 128/92 |
| 4,545,374 A | 10/1985 | Jacobson | 128/303 |
| 4,573,448 A | 3/1986 | Kambin | 128/1 |
| 4,599,086 A | 7/1986 | Doty | 623/17 |
| 4,714,469 A | 12/1987 | Kenna | 623/17 |
| 4,736,738 A | 4/1988 | Lipovsek et al. | 128/92 |
| 4,743,256 A | 5/1988 | Brantigan | 623/17 |
| 4,759,766 A | 7/1988 | Buettner-Janz et al. | 623/17 |
| 4,772,287 A | 9/1988 | Ray et al. | 623/17 |
| 4,820,305 A | 4/1989 | Harms et al. | 623/16 |
| 4,834,757 A | 5/1989 | Brantigan | 623/17 |
| 4,863,476 A | 9/1989 | Shepperd | 623/17 |
| 4,877,020 A | 10/1989 | Vich | 128/92 |
| 4,878,915 A | 11/1989 | Brantigan | 623/17 |
| 4,892,545 A | 1/1990 | Day et al. | 623/17 |
| 4,904,261 A | 2/1990 | Dove et al. | 623/17 |
| 4,917,704 A | 4/1990 | Frey et al. | 623/17 |
| 4,932,975 A | 6/1990 | Main et al. | 623/17 |
| 4,936,848 A | 6/1990 | Bagby | 623/17 |
| 4,961,740 A | 10/1990 | Ray et al. | 606/61 |
| 5,002,576 A | 3/1991 | Fuhrmann et al. | 623/17 |
| 5,015,247 A | 5/1991 | Michelson | 606/61 |
| 5,055,104 A | 10/1991 | Ray | 606/61 |
| 5,062,850 A | 11/1991 | MacMillan et al. | 623/17 |
| 5,071,437 A | 12/1991 | Steffee | 623/17 |
| 5,147,404 A | 9/1992 | Downey | 623/17 |
| 5,192,327 A | 3/1993 | Brantigan | 623/17 |
| 5,207,710 A | 5/1993 | Chu | 623/16 |
| 5,236,460 A | 8/1993 | Barber | 623/17 |
| 5,258,029 A | 11/1993 | Chu et al. | 623/16 |
| 5,282,861 A | 2/1994 | Kaplan | 623/16 |
| 5,290,312 A | 3/1994 | Kojimoto et al. | 623/17 |
| 5,306,307 A | 4/1994 | Senter et al. | 623/17 |
| 5,306,309 A | 4/1994 | Wagner et al. | 623/17 |
| 5,306,310 A | 4/1994 | Siebels | 623/17 |
| 5,348,026 A | 9/1994 | Davidson | 128/898 |
| 5,360,430 A | 11/1994 | Lin | 606/61 |
| 5,397,364 A | 3/1995 | Kozak et al. | 623/17 |
| 5,405,391 A | 4/1995 | Hednerson et al. | 623/17 |
| 5,423,816 A | 6/1995 | Lin | 606/61 |
| 5,423,817 A | 6/1995 | Lin | 606/61 |
| 5,425,772 A | 6/1995 | Brantigan | 623/17 |
| 5,439,464 A | 8/1995 | Shapiro | 606/83 |
| 5,443,514 A | 8/1995 | Steffee | 623/17 |
| 5,443,515 A | 8/1995 | Cohen et al. | 623/17 |
| 5,458,638 A | 10/1995 | Kuslich et al. | 623/17 |
| 5,484,437 A | 1/1996 | Michelson | 606/61 |
| 5,489,307 A | 2/1996 | Kuslich et al. | 623/17 |
| 5,489,308 A | 2/1996 | Kuslich et al. | 623/17 |
| 5,505,732 A | 4/1996 | Michelson | 606/61 |
| 5,507,813 A | 4/1996 | Dowd et al. | 623/16 |
| 5,514,180 A | 5/1996 | Heggeness et al. | 623/17 |
| 5,562,736 A | 10/1996 | Ray et al. | 623/17 |
| D377,095 S | 12/1996 | Michelson | D24/155 |
| D377,096 S | 12/1996 | Michelson | D24/155 |
| 5,591,235 A | 1/1997 | Kuslich | 623/17 |
| 5,593,409 A | 1/1997 | Michelson | 606/61 |
| 5,601,556 A | 2/1997 | Pisharodi | 606/61 |
| 5,609,635 A | 3/1997 | Michelson | 623/17 |
| 5,609,636 A | 3/1997 | Kohrs et al. | 623/17 |
| 5,645,598 A | 7/1997 | Brosnahan, III | 623/17 |
| 5,658,285 A | 8/1997 | Marnay et al. | 606/61 |
| 5,669,909 A | 9/1997 | Zdeblick et al. | 606/61 |
| 5,683,394 A | 11/1997 | Rinner | 606/86 |
| 5,683,463 A | 11/1997 | Godefroy et al. | 623/17 |
| 5,766,252 A | 6/1998 | Henry et al. | 623/17 |
| 5,766,253 A | 6/1998 | Brosnahan, III | 623/17 |
| 5,860,973 A | 1/1999 | Michelson | 606/61 |
| 5,888,224 A | 3/1999 | Beckers et al. | 623/17 |
| 5,906,616 A | 5/1999 | Pavlov et al. | 606/61 |

FOREIGN PATENT DOCUMENTS

| | | | |
|---|---|---|---|
| WO | WO 90/00037 | 1/1990 | A61F/2/44 |
| WO | WO 91/06261 | 5/1991 | A61F/2/44 |
| WO | WO 92/14423 | 9/1992 | A61F/2/44 |
| WO | WO 94/11040 | 5/1994 | A61M/5/178 |
| WO | WO 95/08306 | 3/1995 | A61F/2/44 |
| WO | WO 95/15133 | 6/1995 | A61F/2/44 |
| WO | WO 96/22747 | 8/1996 | A61F/2/44 |

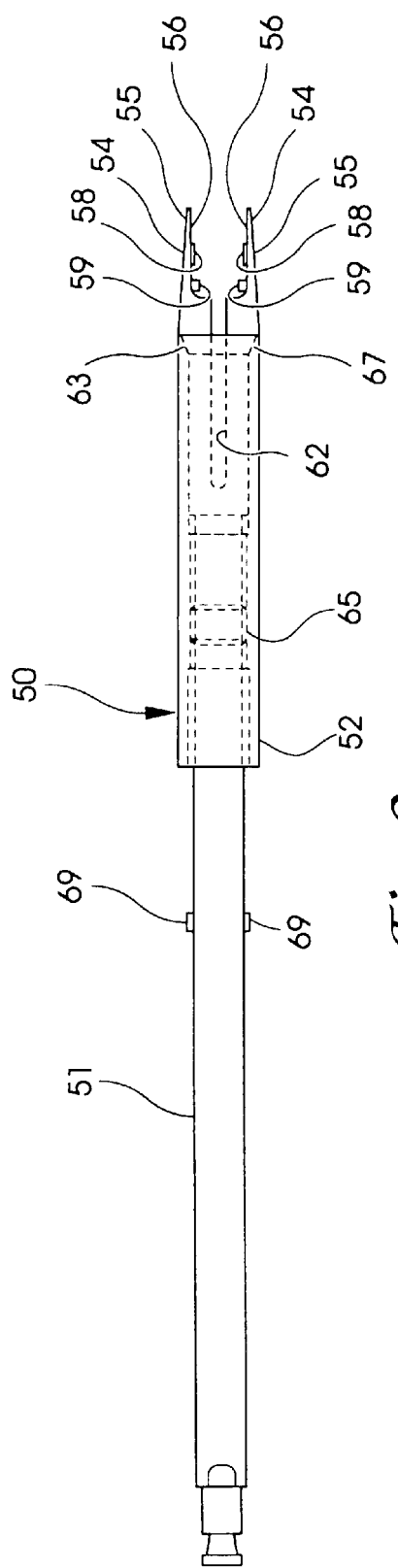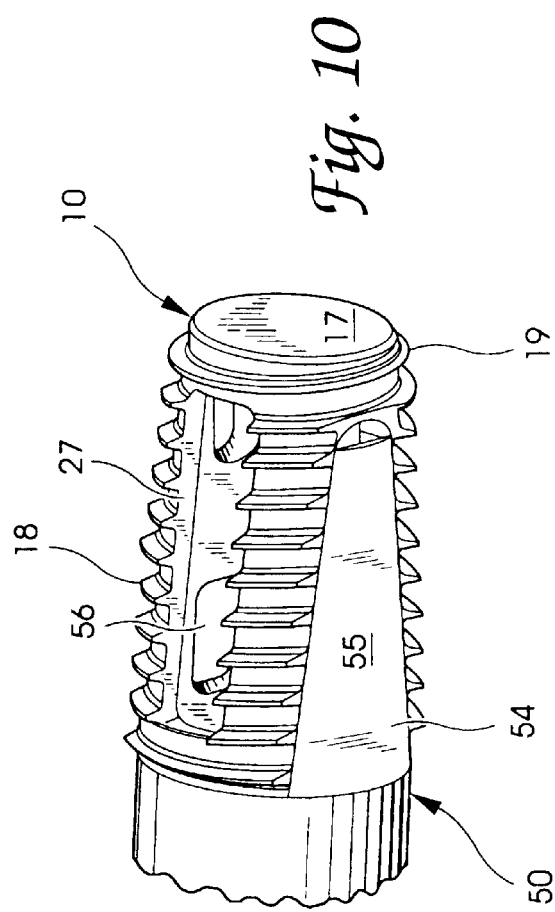

INTERBODY FUSION DEVICE AND METHOD FOR RESTORATION OF NORMAL SPINAL ANATOMY

This application is a con of patent application Ser. No. 09/209,602, filed Dec. 11, 1998, which is a continuation of U.S. patent application Ser. No. 09/157,735, filed Sep. 21, 1998, which is a continuation of U.S. patent application Ser. No. 09/111,197, filed Jul. 7, 1998, now abandoned, which is a continuation of U.S. patent application Ser. No. 08/882,611, filed Jun. 25, 1997, now abandoned, which is a continuation of U.S. patent application Ser. No. 08/835,306, filed Apr. 7, 1997, now abandoned, which is a continuation of Ser. No. 08/413,453, filed Mar. 30, 1995, now U.S. Pat. No. 5,669,909, issued Sep. 23, 1997, which is a continuation-in-part of Ser. No. 08/411,017, filed Mar. 27, 1995, now U.S. Pat. No. 5,782,919, issued Jul. 21, 1998.

BACKGROUND OF THE INVENTION

The present invention relates to an artificial implant to be placed into the intervertebral space left after the removal of a damaged spinal disc. Specifically, the invention concerns an implant that facilitates arthrodesis or fusion between adjacent vertebrae while also maintaining or restoring the normal spinal anatomy at the particular vertebral level.

The number of spinal surgeries to correct the causes of low back pain has steadily increased over the last several years. Most often, low back pain originates from damage or defects in the spinal disc between adjacent vertebrae. The disc can be herniated or can be suffering from a variety of degenerative conditions, so that in either case the anatomical function of the spinal disc is disrupted. The most prevalent surgical treatment for these types of conditions has been to fuse the two vertebrae surrounding the affected disc. In most cases, the entire disc will be removed, except for the annulus, by way of a discectomy procedure. Since the damaged disc material has been removed, something must be positioned within the intra-discal space, otherwise the space may collapse resulting in damage to the nerves extending along the spinal column.

In order to prevent this disc space collapse, the intra-discal space is filled with bone or a bone substitute in order to fuse the two adjacent vertebrae together. In early techniques, bone material was simply disposed between the adjacent vertebrae, typically at the posterior aspect of the vertebrae, and the spinal column was stabilized by way of a plate or a rod spanning the affected vertebrae. With this technique once fusion occurred the hardware used to maintain the stability of the segment became superfluous. Moreover, the surgical procedures necessary to implant a rod or plate to stabilize the level during fusion were frequently lengthy and involved.

It was therefore determined that a more optimum solution to the stabilization of an excised disc space is to fuse the vertebrae between their respective end plates, most optimally without the need for anterior or posterior plating. There have been an extensive number of attempts to develop an acceptable intra-discal implant that could be used to replace a damaged disc and yet maintain the stability of the disc interspace between the adjacent vertebrae, at least until complete arthrodesis is achieved. These "interbody fusion devices" have taken many forms. For example, one of the more prevalent designs takes the form of a cylindrical implant. These types of implants are represented by the patents to Bagby, No. 4,501,269; Brantigan, No. 4,878,915; Ray, Nos. 4,961,740 and 5,055,104; and Michelson, No. 5,015,247. In these cylindrical implants, the exterior portion of the cylinder can be threaded to facilitate insertion of the interbody fusion device, as represented by the Ray, Brantigan and Michelson patents. In the alternative, some of the fusion implants are designed to be pounded into the intra-discal space and the vertebral end plates. These types of devices are represented by the patents to Brantigan, Nos. 4,743,256; 4,834,757 and 5,192,327.

In each of the above listed patents, the transverse cross section of the implant is constant throughout its length and is typically in the form of a right circular cylinder. Other implants have been developed for interbody fusion that do not have a constant cross section. For instance, the patent to McKenna, No. 4,714,469 shows a hemispherical implant with elongated protuberances that project into the vertebral end plate. The patent to Kuntz, No. 4,714,469, shows a bullet shaped prosthesis configured to optimize a friction fit between the prosthesis and the adjacent vertebral bodies. Finally, the implant of Bagby, No. 4,936,848 is in the form of a sphere which is preferably positioned between the centrums of the adjacent vertebrae.

Interbody fusion devices can be generally divided into two basic categories, namely solid implants and implants that are designed to permit bone ingrowth. Solid implants are represented by U.S. Pat. Nos. 4,878,915; 4,743,256; 4,349,921 and 4,714,469. The remaining patents discussed above include some aspect that permits bone to grow across the implant. It has been found that devices that promote natural bone ingrowth achieve a more rapid and stable arthrodesis. The device depicted in the Michelson patent is representative of this type of hollow implant which is typically filled with autologous bone prior to insertion into the intra-discal space. This implant includes a plurality of circular apertures which communicate with the hollow interior of the implant, thereby providing a path for tissue growth between the vertebral end plates and the bone or bone substitute within the implant. In preparing the intra-discal space, the end plates are preferably reduced to bleeding bone to facilitate this tissue ingrowth. During fusion, the metal structure provided by the Michelson implant helps maintain the patency and stability of the motion segment to be fused. In addition, once arthrodesis occurs, the implant itself serves as a sort of anchor for the solid bony mass.

A number of difficulties still remain with the many interbody fusion devices currently available. While it is recognized that hollow implants that permit bone ingrowth into bone or bone substitute within the implant is an optimum technique for achieving fusion, most of the prior art devices have difficulty in achieving this fusion, at least without the aid of some additional stabilizing device, such as a rod or plate. Moreover, some of these devices are not structurally strong enough to support the heavy loads and bending moments applied at the most frequently fused vertebral levels, namely those in the lower lumbar spine.

There has been a need for providing an interbody fusion device that optimizes the bone ingrowth capabilities but is still strong enough to support the spine segment until arthrodesis occurs. It has been found by the present inventors that openings into a hollow implant for bone ingrowth play an important role in avoiding stress shielding of the autologous bone impacted within the implant. In other words, if the ingrowth openings are improperly sized or configured, the autologous bone will not endure the loading that is typically found to be necessary to ensure rapid and complete fusion. In this instance, the bone impacted within the implant may resorb or evolve into simply fibrous tissue, rather than a bony fusion mass, which leads to a generally unstable construction. On the other hand, the bone ingrowth openings must not be so extensive that the cage provides insufficient support to avoid subsidence into the adjacent vertebrae.

Another problem that is not addressed by the above prior devices concerns maintaining or restoring the normal anatomy of the fused spinal segment. Naturally, once the disc is removed, the normal lordotic or kyphotic curvature of the spine is eliminated. With the prior devices, the need to restore this curvature is neglected. For example, in one type of commercial device, the BAK device of SpineTech, as represented by the patent to Bagby, No. 4,501,269, the adjacent vertebral bodies are reamed with a cylindrical reamer that fits the particular implant. In some cases, the normal curvature is established prior to reaming and then the implant inserted. This type of construct is illustrated in FIG. 1 which reveals the depth of penetration of the cylindrical implant into the generally healthy vertebrae adjacent the instrumented discal space. However, this over-reaming of the posterior portion is generally not well accepted because of the removal of load bearing bone of the vertebrae,. and because it is typically difficult to ream through the posterior portion of the lower lumbar segment where the lordosis is greatest. In most cases using implants of this type, no effort is made to restore the lordotic curvature, so that the cylindrical implant is likely to cause a kyphotic deformity as the vertebra settles around the implant. This phenomenon can often lead to revision surgeries because the spine becomes imbalanced.

In view of these limitations of the prior devices, there remains a need for an interbody fusion device that can optimize bone ingrowth while still maintaining its strength and stability. There is further a need for such an implant that is capable of maintaining or restoring the normal spinal anatomy at the instrumented segment. This implant must be strong enough to support and withstand the heavy loads generated on the spine at the instrumented level, while remaining stable throughout the duration.

SUMMARY OF THE INVENTION

In response to the needs still left unresolved by the prior devices, the present invention contemplates a hollow threaded interbody fusion device configured to restore the normal angular relation between adjacent vertebrae. In particular, the device includes an elongated body, tapered along substantially its entire length, defining a hollow interior and having an outer diameter greater than the size of the space between the adjacent vertebrae. The body includes an outer surface with opposite tapered cylindrical portions and a pair of opposite flat tapered side surfaces between the cylindrical portions. Thus, at an end view, the fusion device gives the appearance of a cylindrical body in which the sides of the body have been truncated along a chord of the body's outer diameter. The cylindrical portions are threaded for controlled insertion and engagement into the end plates of the adjacent vertebrae.

In another aspect of the invention, the outer surface is tapered along its length at an angle corresponding, in one embodiment, to the normal lordotic angle of lower lumbar vertebrae. The outer surface is also provided with a number of vascularization openings defined in the flat side surfaces, and a pair of elongated opposite bone ingrowth slots defined in the cylindrical portions. The bone ingrowth slots have a transverse width that is preferably about half of the effective width of the cylindrical portions within which the slots are defined.

In another embodiment, the interbody fusion device retains the same tapered configuration of the above embodiment, along with the truncated sidew walls and interrupted external threads. However, in this embodiment, the implant is not hollow but is instead solid. Bone ingrowth is achieved by forming the solid tapered implant of a porous high strength material tht permits bone ingrowth into interconnected pores while retaining sufficient material for structural stability in situ. In one preferred embodiment, the material is porous tantalum.

A driving tool is provided for inserting the fusion device within the intra-discal space. In one feature, the driving tool includes a shaft having a pair of opposite tapered tongs situated at one end. The tongs are connected to the shaft by way of a hinge slot that biases the tongs apart to receive a fusion device therebetween. The driving tool is further provided with a sleeve concentrically disposed about the shaft and configured to slide along the shaft and compress the hinge to push the tongs together to grip the fusion device. Alternatively, an internal expanding collet may be used to internally hold the fusion device securely during insertion.

In one aspect of the driving tool, the tapered tongs have an outer surface that takes on the form of the tapered cylindrical portions of the fusion device. The tongs also have a flat inward facing surface to correspond to the flat side surfaces of the fusion device. Thus, when the tongs are compressed against the fusion device, the inward facing surfaces of the tongs contact the flat sides of the fusion device and the outer surface of the tongs complete the conical form of the fusion device to facilitate screw-in insertion. The inward facing surface of the tongs may also be provided with projections to engage openings in the fusion device to permit driving and rotation of the device within the intra-discal space.

In another aspect of the invention, methods are provided for implanting the fusion device between adjacent vertebrae. In one method, the approach is anterior and includes the steps of dilating the disc space and drilling the end plates of the adjacent vertebrae to the minor diameter of the fusion device threads. A sleeve is inserted to provide a working channel for the drilling step and the subsequent step of implanting the fusion device. The implant is engaged with the driving tool, inserted through the sleeve and threaded into the prepared bore. The depth of insertion of the tapered fusion device determines the amount of angular separation achieved for the adjacent vertebrae.

In another inventive method, the insertion site is prepared posteriorly, namely the disc space is dilated and a minor diameter hole is drilled into the vertebral end plates. A sleeve is also arranged to provide a working channel for the drilling and insertion steps. The fusion device is inserted into the drilled hole with the flat side walls facing the adjacent vertebra. The device is then rotated so that the external threads on the cylindrical portion cut into and engage the adjacent vertebrae. In addition, since the fusion device is tapered, the tapered outer surface of the device will angularly separate the adjacent vertebrae to restore the normal anatomic lordosis.

DESCRIPTION OF THE FIGURES

FIG. 9 is a top-elevational view of an implant driver according to another aspect of the present invention.

FIG. 10 is an enlarged perspective view of the end of the implant driver engaged about an interbody fusion device, as depicted in FIG. 2.

DESCRIPTION OF THE PREFERRED EMBODIMENTS

Figure 1:
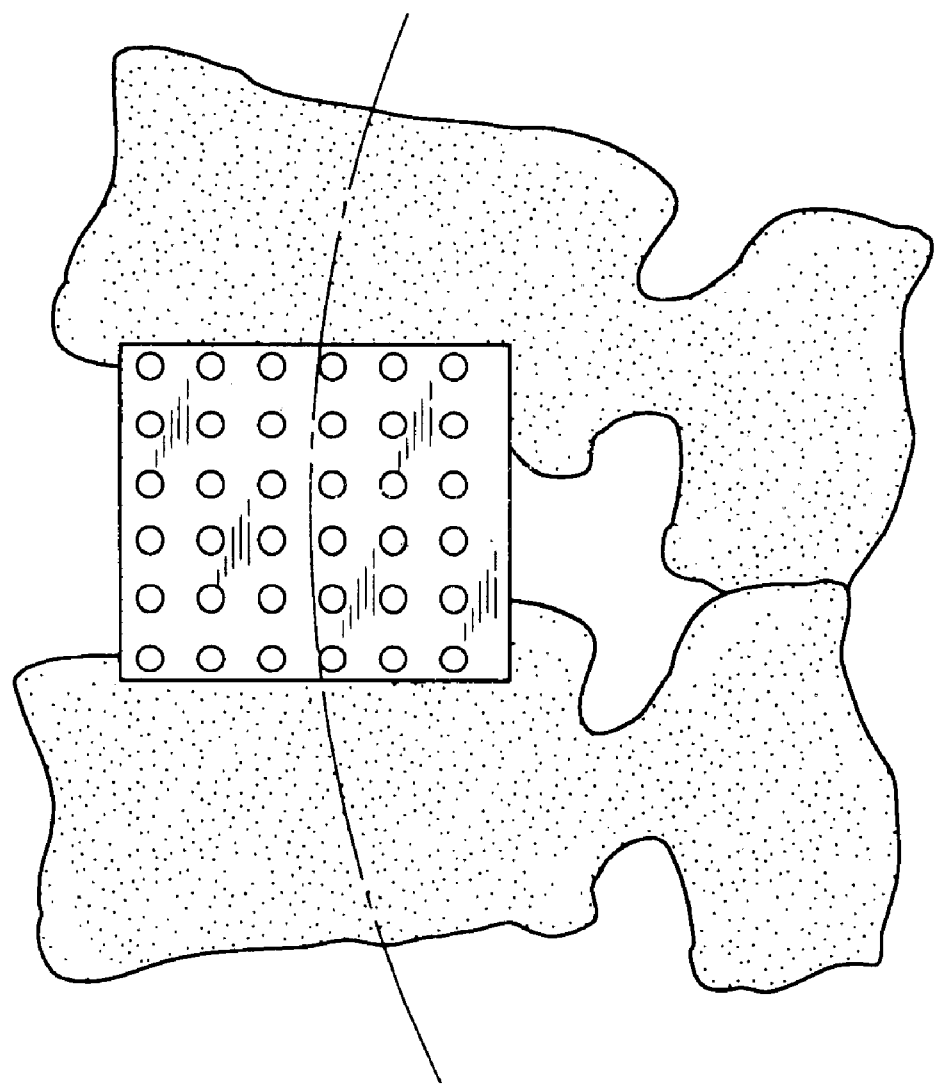
FIG. 1 is a side-elevational view in the sagittal plane of a fusion device of the prior art.
Figure 5:
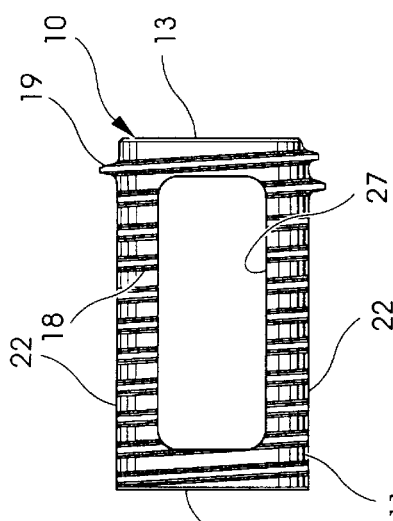
FIG. 5 is a top-elevational view of the interbody fusion device shown in FIG. 2.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

An interbody fusion device 10 in accordance with one aspect of the present invention is shown in FIGS. 2–5. The device is formed by a solid conical body 11, that is preferably formed of a biocompatible or inert material. For example, the body 11 can be made of a medical grade stainless steel or titanium, or other suitable material having adequate strength characteristics set forth herein. The device may also be composed of a biocompatible porous material, such as porous tantalum provided by Implex Corp. For purposes of reference, the device 10 has an anterior end 12 and a posterior end 13, which correspond to the anatomic position of the device 10 when implanted in the intra-discal space. The conical body 11 defines a hollow interior 15 which is bounded by a body wall 16 and closed at the posterior end 13 by an end wall 17 (see FIG. 3). The hollow interior 15 of the device 10 is configured to receive autograft bone or a bone substitute material adapted to promote a solid fusion between adjacent vertebrae and across the intra-discal space.

In accordance with the invention, the interbody fusion device 10 is a threaded device configured to be screw threaded into the end plates of the adjacent vertebrae. In one embodiment of the invention, the conical body 11 defines a series of interrupted external threads 18 and a complete thread 19 at the leading end of the implant. The complete thread 19 serves as a "starter" thread for screwing the implant into the vertebral endplates at the intra-discal space. The threads 18 and 19 can take several forms known in the art for engagement into vertebral bone. For instance, the threads can have a triangular cross-section or a truncated triangular cross-section. Preferably, the threads have a height of 1.0 mm (0.039 in) in order to provide adequate purchase in the vertebral bone so that the fusion device 10 is not driven out of the intra-discal space by the high loads experienced by the spine. The thread pitch in certain specific embodiments can be 2.3 mm (0.091 in) or 3.0 mm (0.118 in), depending upon the vertebral level at which the device 10 is to be implanted and the amount of thread engagement necessary to hold the implant in position.

Figure 4:
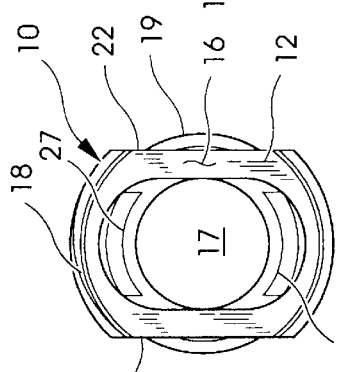
FIG. 4 is an end elevational view from the anterior end of the interbody fusion device shown in FIG. 2.

In one aspect of the invention, the conical body 11, and particularly the body wall 16, includes parallel truncated side walls 22, shown most clearly in FIG. 4. The side walls are preferably flat to facilitate insertion of the fusion device between the end plates of adjacent vertebrae and provide area between for bony fusion. The truncated side walls extend from the anterior end 12 of the device up to the complete threads 19 at the posterior end 13. Thus, with the truncated side walls 22, the device 10 gives the appearance at its end view of an incomplete circle in which the sides are cut across a chord of the circle. In one specific example, the interbody fusion device 10 has a diameter at its anterior end of 16.0 mm (0.630 in). In this specific embodiment, the truncated side walls 22 are formed along parallel chord lines approximately 12.0 mm (0.472 in) apart, so that the removed arc portion of the circle roughly subtends 90° at each side of the device. Other benefits and advantages provided by the truncated side walls 22 of the fusion device 10 will be described in more detail herein.

The conical body 11 of the device 10 includes a pair of vascularization openings 24 and 25 defined through each of the truncated side walls 22. These openings 24 and 25 are adapted to be oriented in a lateral direction or facing the sagittal plane when the fusion device is implanted within the intra-discal space. The openings are intended to provide a passageway for vascularization to occur between the bone implant material within the hollow interior 15 and the surrounding tissue. In addition, some bone ingrowth may also occur through these openings. The openings 24 and 25 have been sized to provide optimum passage for vascularization to occur, while still retaining a significant amount of structure in the conical body 11 to support the high axial loads passing across the intra-discal space between adjacent vertebrae.

The conical body 11 also defines opposite bone ingrowth slots 27, each of which are oriented at 90° to the truncated side walls 22. Preferably, these slots 27 are directly adjacent the vertebral end plates when the device 10 is implanted. More particularly, as the threads 18 and 19 of the device are screwed into the vertebral endplates, the vertebral bone will extend partially into the slots 27 to contact bone implant material contained within the hollow interior 15 of the device 10. As shown more clearly in FIG. 5, the bone ingrowth slots 27 are configured to provide maximum opening for bone ingrowth, in order to ensure complete arthrodesis and a solid fusion. Preferably, the slots have a lateral width that approximates the effective width of the threaded portions of the body. It has been found that the prior devices which utilize a plurality of small apertures do not promote a rapid and solid arthrodesis of the bone material. Instead, the smaller apertures often lead to pseudo-arthrosis and the generation of fibrous tissue. Since the bone ingrowth slots 27 of the present invention are directly facing the vertebrae, they are not situated in a portion of the device that must bear high loads. Instead, the truncated side walls 22 will bear most of the load passing between the vertebral end plates through the interrupted threads 18 and across the intra-discal space.

In a further feature, the anterior end 12 of the body wall 16 can define a pair of diametrically opposed notches 29, which are configured to engage an implant driver tool as described herein. Moreover, the end wall 17 at the posterior end 13 of the implant can be provided with a tool engagement feature (not shown). For example, a hex recess can be provided to accommodate a hex driver tool, as described further herein.

Figure 3:
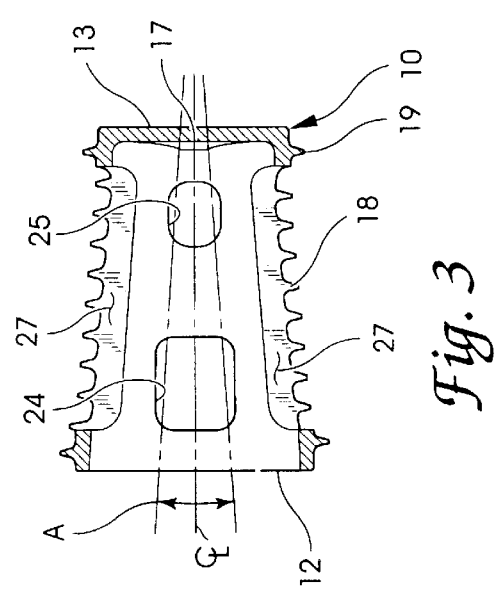
FIG. 3 is a side cross-sectional view of the interbody fusion device shown in FIG. 2, taken along line 3—3 as viewed in the direction of the arrows.
Figure 2:
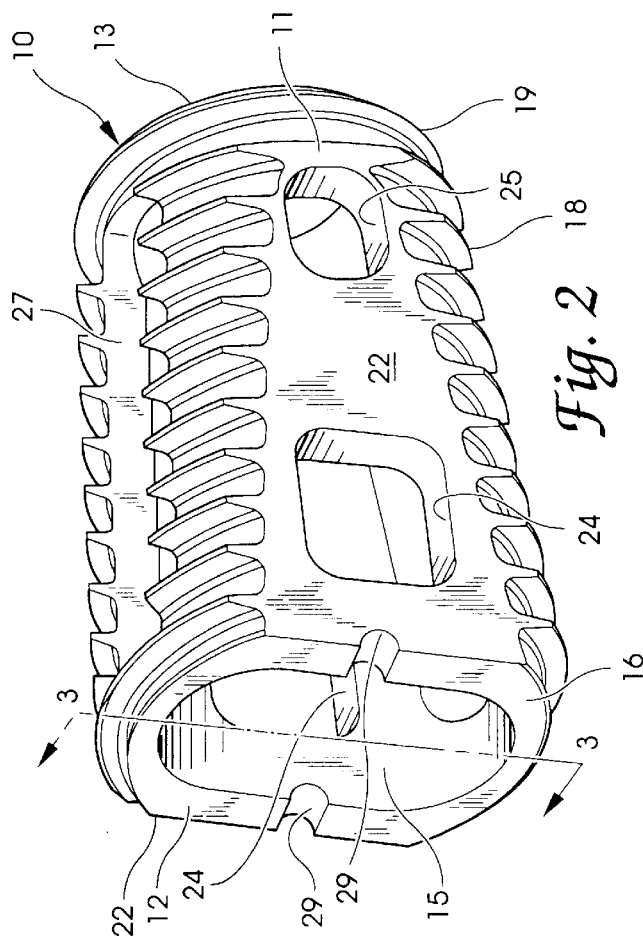
FIG. 2 is an enlarged perspective view of an interbody fusion device according to one embodiment of the present invention.

In one important feature of the interbody fusion device of the present invention, the body 11 includes a tapered or conical form. In other words, the outer diameter of the device at its anterior end 12 is larger than the outer diameter at the posterior end 13. As depicted in FIG. 3, the body wall 16 tapers at an angle A about the centerline CL of the device 10. The taper of the body wall 16 is adapted to restore the normal relative angle between adjacent vertebrae. For example, in the lumbar region, the angle A is adapted to restore the normal lordotic angle and curvature of the spine in that region. In one specific example, the angle A is 8.794°. It is understood that the implant may have non-tapered portions, provided that the portions do not otherwise interfere with the function of the tapered body.

Figure 7:
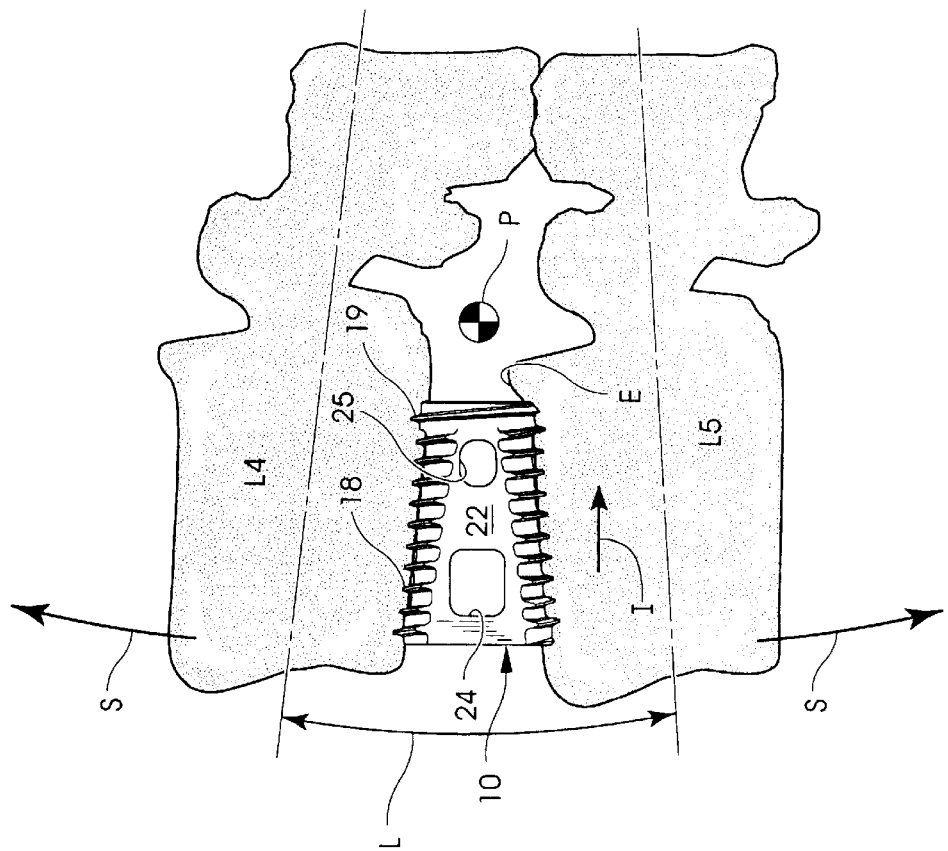
FIG. 7 is a sagittal plane view of the interbody fusion device implanted between L4 and L5 shown in FIG. 6.

The taper angle A of the implant, coupled with the outer diameter at the anterior and posterior ends of the fusion device 10, define the amount of angular spreading that will occur between the adjacent vertebrae as the implant is placed or screwed into position. This feature is depicted more clearly in FIGS. 6 and 7 in which a preferred construct employing a pair of fusion devices 10 is shown. In the depicted construct, the devices 10 are disposed between the lower lumbar vertebrae L4 and L5, with the threads 18 and 19 threaded into the end plates E of the two vertebrae. As shown in FIG. 7, as the device 10 is threaded into the end plates E, it advances in the direction of the arrow I toward the pivot axis P of the vertebral level. The pivot axis P is nominally the center of relative rotation between the adjacent vertebrae of the motion segment. As the tapered fusion device 10 is driven further in the direction of the arrow I toward the pivot axis P, the adjacent vertebrae L4 and L5 are angularly spread in the direction of the arrows S. Depth of insertion of the fusion device 10 will determine the ultimate lordotic angle L achieved between the two vertebrae.

In specific embodiments of the implant 10, the outer diameter or thread crest diameter at the anterior end 12 can be 16, 18 or 20 mm, and the overall length of the device 26 mm. The sizing of the device is driven by the vertebral level into which the device is implanted and the amount of angle that must be developed.

Figure 6:
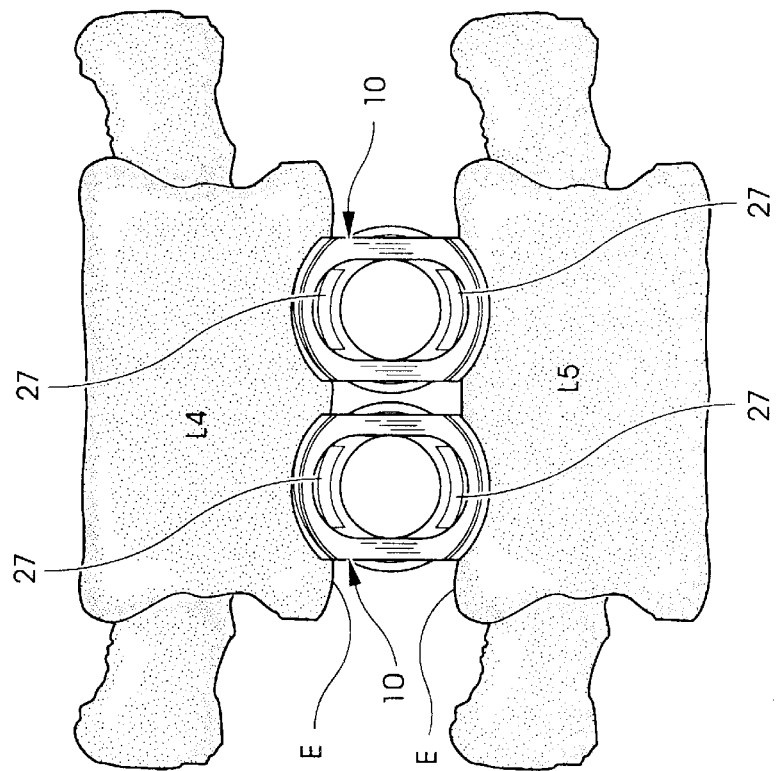
FIG. 6 is an A-P lateral view from the anterior aspect of the spine showing two interbody fusion devices according to FIG. 2 implanted within the interbody space between L4 and L5.

In another aspect of the invention, device 10 is sized so that two such cylindrical bodies 11 can be implanted into a single disc space, as shown in FIG. 6. This permits the placement of additional bone graft material between and around the devices 10 in situ. This aspect further promotes fusion across the intra-discal space and also serves to more firmly anchor the devices between the adjacent vertebrae to prevent expulsion due to the high axial loads at the particular vertebral level.

In one specific embodiment of the interbody fusion device 10, the vascularization opening 24 is generally rectangular in shape having dimensions of 6.0 mm (0.236 in) by 7.0 mm (0.276 in). Similarly, the vascularization opening 25 is rectangular with dimensions of 4.0 mm (0.157 in) by 5.0 mm (0197 in). Naturally, this opening is smaller because it is disposed at the smaller posterior end 13 of the device 10. The bone ingrowth slots 27 are also rectangular in shape with a long dimension of 20.0 mm (0.787 in) and a width of 6.0 mm (0.236 in). It has been found that these dimensions of the vascularization openings 24, 25 and slots 27 provide optimum bone ingrowth and vascularization. In addition, these openings are not so large that they compromise the structural integrity of the device or that they permit the bone graft material contained within the hollow interior 15 to be easily expelled during implantation.

As can be seen in FIG. 7, when the device is in position between the L4 and L5 vertebrae, the vascularization openings 24 and 25 are side facing to contact the highly vascularized tissue surrounding the vertebrae. In addition, as can be seen in FIG. 6, the bone ingrowth slots 27 are axially directed so that they contact the vertebral end plates E.

Figure 8:
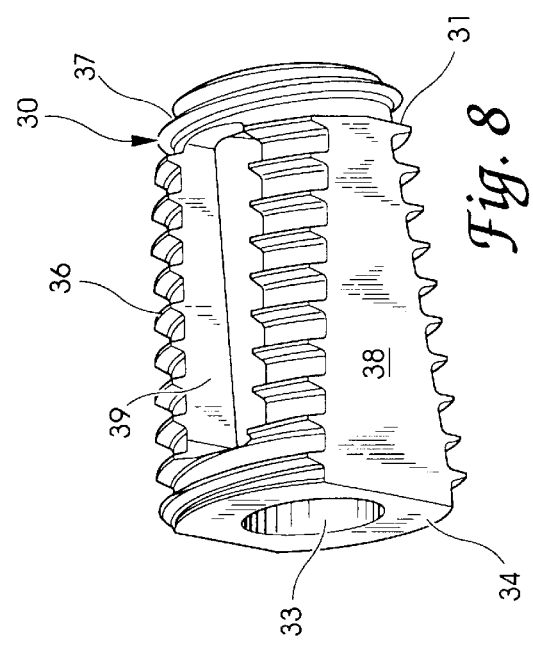
FIG. 8 is a perspective view of an alternative embodiment of the interbody fusion device according to the present invention.

In an alternative embodiment of the invention, shown in FIG. 8, an interbody fusion device 30 is formed of a conical body 31. The body wall 34 defines a hollow interior 33 as with the fusion device 10 of the previous embodiment. However, in this embodiment the truncated side wall 38 does not include any vascularization openings. Moreover, the bone ingrowth slots 39 on opposite sides of the device 30 are smaller. This means that the interrupted threads 36 on the exterior of the device 30 extend a greater length around the implant. Such a design could be utilized if a porous material (e.g., porous tantalum) were used to provide additional surface area for tissue ingrowth and anchorage to the adjacent bone. Also, this interbody fusion device 30 of the embodiment shown in FIG. 8 can have application at certain vertebral levels where the risk of expulsion of the device is greatest. Consequently, the amount of thread contact is increased to prevent such expulsion. Prior to insertion, the hollow interior 15 of the fusion device 10 is filled completely with bone or substitute to facilitate this pre-loading.

Figure 8A:
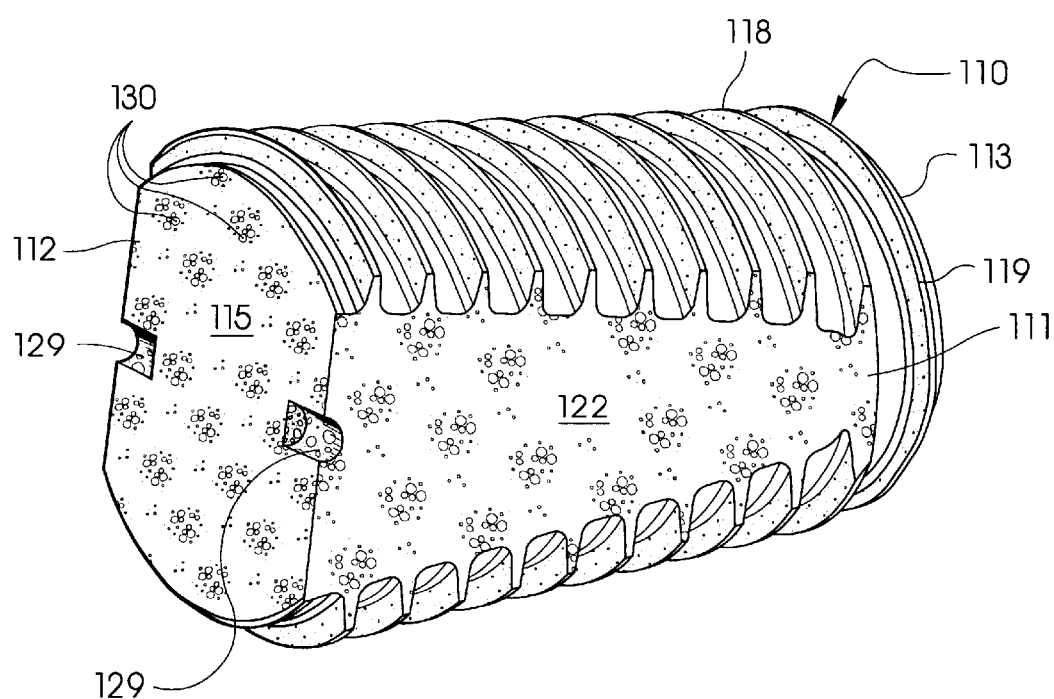
FIG. 8A is a perspective view of another embodiment of a tapered interbody fusion device according to the present invention.

In a further embodiment using a porous material, the interbody fusion device 110 of FIG. 8A retains the tapered configuration of the previous embodiments, but is solid instead of hollow. The device 110 comprises a tapered body 111 having an larger outer diameter at its anterior end 112 than at its posterior end 113. The entire body 111 is solid leaving a closed surface, such as surface 115, at both ends of the implant. The device includes the interrupted threads 118, starter threads 119 and truncated side walls 122 of the prior embodiments. A driving tool slot 129 can also be defined in the end surface 115. Alternatively, the starter threads 119 can be eliminated leaving an unthreaded cylindrical portion at the posterior end of the implant. Similarly, the driving tool slot 129 take on many configurations depending upon the design of the tool used to insert the device 110 into the intradiscal space.

The benefits of the embodiment of the fusion device shown in FIG. 8A are especially appreciated by the use of a porous, high strength material to form the solid body 111. In the preferred embodiment, this material is a porous tantalum-carbon composite marketed by Implex Corp. under the tradename HEDROCEL® and described in U.S. Pat. No. 5,282,861 to Kaplan, which description is incorporated herein by reference. Due to the nature of the HEDROCEL® material, the entire exterior surface of the solid body 111 includes pores 130 that are interconnected throughout the body. The substrate of the HEDROCEL® carbon-tantalum composite is a skeleton of vitreous carbon, or a reticulated open cell carbon foam, which defines a network of interconnecting pores. The substrate is infiltrated with a thin film of tantalum.

HEDROCEL® is preferred because it provides the advantages of both metal and ceramic implants without the corresponding disadvantages. HEDROCEL is well suited for the interbody fusion device of the present invention because it mimics the structure of bone and has a modulus of elasticity that approximates that of human bone. The interconnected porosity encourages bone ingrowth and eliminates dead ends which limit vascular support for the bone. The infiltrated metal film provides strength and stiffness without significant weight increase. A HEDROCEL® implant is sufficiently strong to maintain the intervertebral space and normal curvature of the spine at the instrumented motion segment. At the same time, stress shielding is avoided. This composite material is also advantageous because it eliminates the need for allografts or autografts.

One additional advantage of this material is that it does not undergo resorption. This prevents early degradation which can inhibit bone regeneration. A non-resorbable implant is also beneficial where complete bone ingrowth cannot be achieved. Disadvantages of permanent, nonresorbable implants, however, are avoided because of the biocompatibility and osteoconductivity of the composite.

While HEDROCEL® is preferred, it is contemplated that any suitable high strength porous material may be used. Other open-celled substrates and metals are contemplated. For example, the substrate may be other carbonaceous materials, such as graphite, or ceramics, such as tricalcium phosphate or calcium aluminate. Any suitable metal is contemplated, but Group VB elements, such as tantalum and niobium, and their alloys, are preferred. Tantalum is particularly preferred for its good mechanical properties and biocompatibility.

The interbody fusion device 10 can be implanted using an implant driver 50, shown in FIG. 9, according to one aspect of the invention. The implant driver 50 is comprised of a shaft 51 and sleeve 52 concentrically disposed about the shaft. Tongs 54 are formed at one end of the shaft for gripping the interbody fusion device 10 for implantation. The tongs include a tapered outer surface 55 and an opposite flat inner surface 56 adapted to engage the truncated side walls 22 of the interbody fusion device. The tapered outer surface 55 conforms to the root diameter of the interrupted threads 18 so that the tongs 54 essentially complete the full cylindrical shape of the body wall 16. The adaptation of the tong's tapered outer surface 55 facilitates screw insertion of the interbody fusion device 10 since the outer surface 55 will ride within the tapped bore in the vertebral endplates.

Each of the tongs is provided with interlocking fingers 58 and a driving projection 59 extending from the inner surface 56. The function of these components is shown more clearly with reference to FIG. 11. Referring first to FIG. 9, the shaft 51 defines a hinge slot 62 supporting each of the pair of tongs 54. The hinge slot 62 is configured so that the tongs will have a naturally biased position spread sufficiently apart to accept the tapered interbody fusion device 10 therebetween. The shaft 51 defines a conical taper 63 between the hinged slot 62 and each of the tongs 54. This conical taper mates with a conical chamfer 67 defined on the inner wall of the sleeve 52. Thus, as the sleeve 52 is advanced toward the tongs 54, the conical chamfer 67 rides against the conical taper 63 to close or compress the hinge slot 62. In this manner, the tongs 54 are pushed toward each other and pressed into gripping engagement with the interbody fusion device situated between the tongs.

The shaft 51 and sleeve 52 are provided with a threaded interface 65 which permits the sleeve 52 to be threaded up and down the length the shaft. Specifically, the threaded interface 65 includes external threads on the shaft 51 and internal threads on the sleeve 52 having the same pitch so that the sleeve can be readily moved up and down the implant driver 50. The shaft 51 is also provided with a pair of stops 69 which restrict the backward movement of the sleeve 52 to only the extent necessary to allow the tongs 54 to separate a sufficient distance to accept the interbody fusion device 10.

Figure 11:
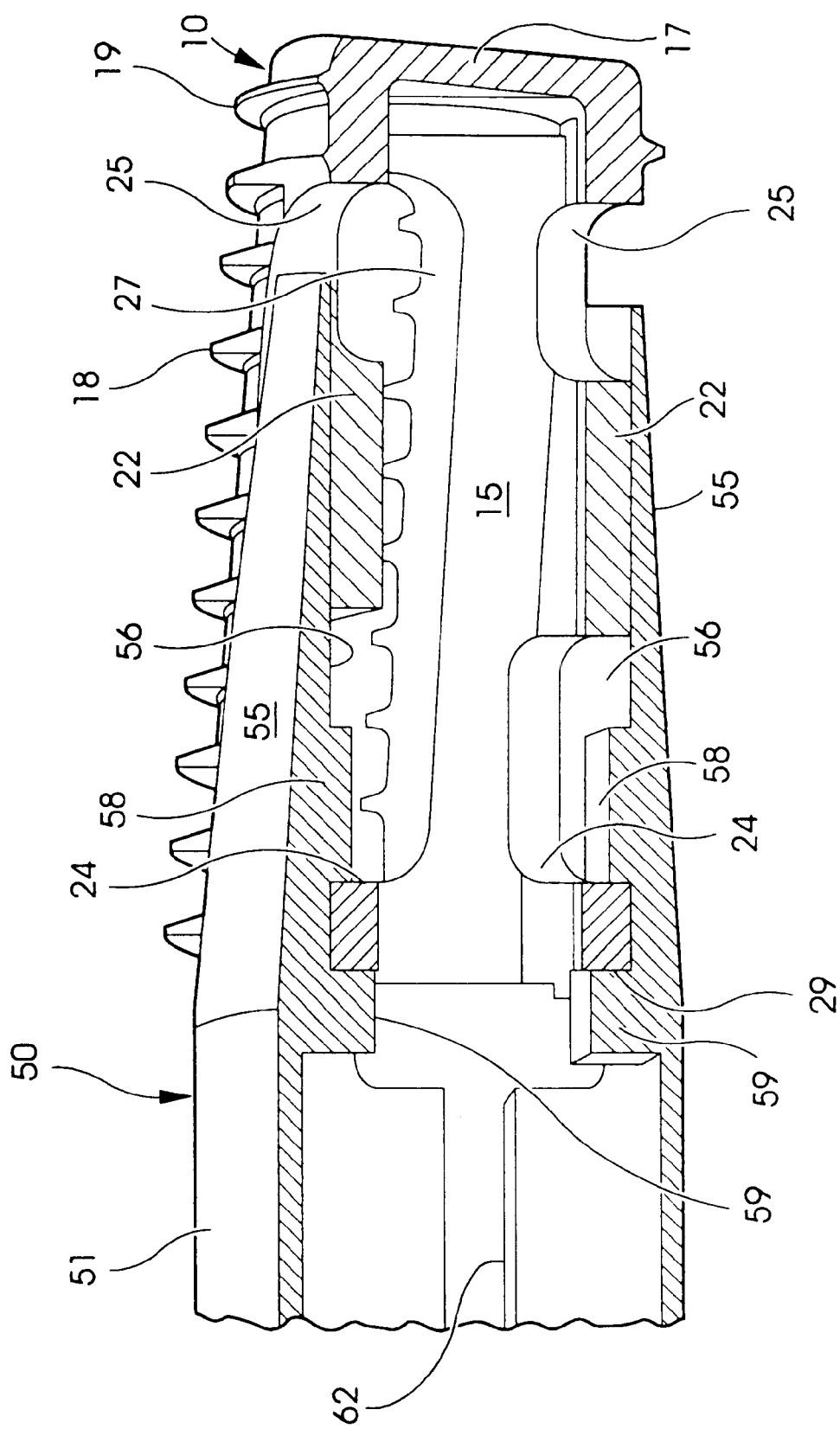
FIG. 11 is an enlarged partial side cross-sectional view showing the implant driver engaging the interbody fusion device, as shown in FIG. 10.

The use of the implant driver 50 is shown with reference to FIGS. 10 and 11. As can be seen in FIG. 10, the outer surface 55 of the tongs 54 reside generally flush with the root diameter of the interrupted threads 18. As seen in FIG. 11, the interlocking fingers 58 can be arranged to fit within the vascularization opening 24 on each of the truncated side walls 22. In a similar fashion, the driving projections 59 engage the driving tool slots 29 at the anterior end 12 of the conical body 11. The combination of the interlocking fingers 58 and driving projections 59 firmly engage the interbody fusion device 10 so that the device can be screw threaded into a tapped or untapped opening in the vertebral bone.

Figure 12:
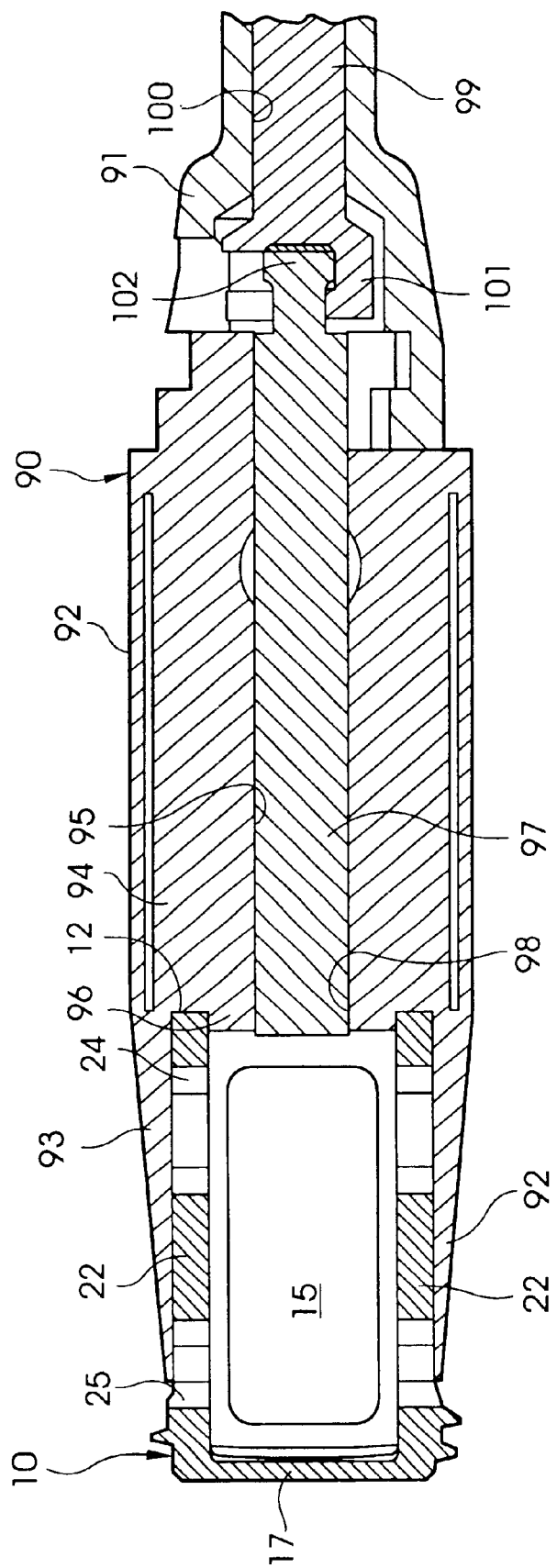
FIG. 12 is an enlarged partial side cross-sectional view showing an implant driver of an alternative embodiment adapted for engaging the interbody fusion device 10.

An alternative embodiment of the implant driver is shown in FIG. 12. The driver 90 includes a shaft 91, having a length sufficient to reach into the intradiscal space from outside the patient. Connected to the end of shaft 91 is a head which defines a pair of opposite tongs 93, each of which are configured for flush contact with the flat truncated side walls 22 of the fusion device 10. Like the tongs 54 of the previously described implant driver 50, the outer surface of the tongs is cylindrical to correspond to the cylindrical threaded portion of the device.

Unlike the implant driver 50, the driver 90 of the embodiment in FIG. 12 uses an expanding collet assembly to firmly grip the fusion device 10 for insertion into the body. Specifically, the head 92 defines a collet 94 having a central collet bore 95 formed therethrough. The collet 94 terminates in an annular flange 96 that at least initially has a diameter slightly smaller than the inner diameter of the fusion device 10 at its end 12. An expander shaft 97 slidably extends through the collet bore and includes a flared tip 98 situated adjacent and extending just beyond the annular flange 96. The flared tip 98 of the expander shaft 97 starts at a diameter sized to slide within the collet bore 95 and gradually flares to a diameter larger than the bore.

The implant driver 90 includes a puller shaft 99 slidably disposed within a bore 100 defined in the shaft 91. The puller shaft 99 has a locking chamber 101 at its end which engages a locking hub 102 formed at the end of the expander shaft 97. The puller shaft 99 projects beyond the end of shaft 91 for access by the surgeon. When the puller shaft 99 is pulled, it pulls the expander shaft 97 away from the annular flange 96 of the collet 94 so that the flared tip 98 becomes progressively engaged within the collet bore 95. As the tip 98 advances further into the bore 95, the annular flange 96 expands from its initial diameter to a larger second diameter sufficient for firm gripping contact with the interior of the fusion device 10. With the fusion device so engaged, the implant driver can be used to insert the device 10 into the surgical site, after which the expander shaft can be advanced beyond the collet bore to release the flared tip and, consequently, the fusion device.

In accordance with the present invention, two methods for implanting the interbody fusion device 10 are contemplated. First, with reference to FIGS. 12(a)–12(d), an anterior approach is shown. As a preliminary step, it is necessary to locate appropriate starting points for implanting the fusion device, preferably bilaterally. In the first step of the anterior approach, a dilator 75 is disposed between the vertebral end plates E to dilate the disc space between the L4 and L5 vertebrae. (It is understood, of course, that this procedure can be applied at other vertebral levels). In the second step, shown in FIG. 12(b), an outer sleeve 76 is disposed about the disc space. The outer sleeve 76 can be of a known design that is configured to positively engage the anterior aspect of the vertebral bodies to firmly, but temporarily, anchor the outer sleeve 76 in position. In essence, this outer sleeve 76 operates as a working channel for this laproscopic-type approach. In this step of FIG. 12(b), a drill 77 of known design is extended through the outer sleeve and used to drill out circular openings in the adjacent vertebral bodies. The openings can be tapped to facilitate screw insertion of the fusion device, although this step is not necessary.

In the next step shown in FIG. 12(c), the fusion device 10 is engaged by the implant driver 50 and extended through the outer sleeve 76 until the starter thread 19 contacts the bone opening. The implant driver 50 can then be used to screw thread the fusion device into the tapped or untapped opening formed in the vertebral end plate E. It is understood that in this step, other suitable driving tools could be used, such as a screw driver type device to engage the driving tool slots 29 at the anterior end 12 of the device 10. As discussed previously, the degree of insertion of the fusion device 10 determines the amount of lordosis added or restored to the vertebral level. In the final step, the implant driver is removed leaving the fusion device 10 in position. It can be seen that once implanted, the closed end wall 17 is directed toward the posterior aspect of the vertebrae. The hollow interior 15 is open at its anterior end, but can be closed by a plastic or metal material, if necessary.

Figure 13A:
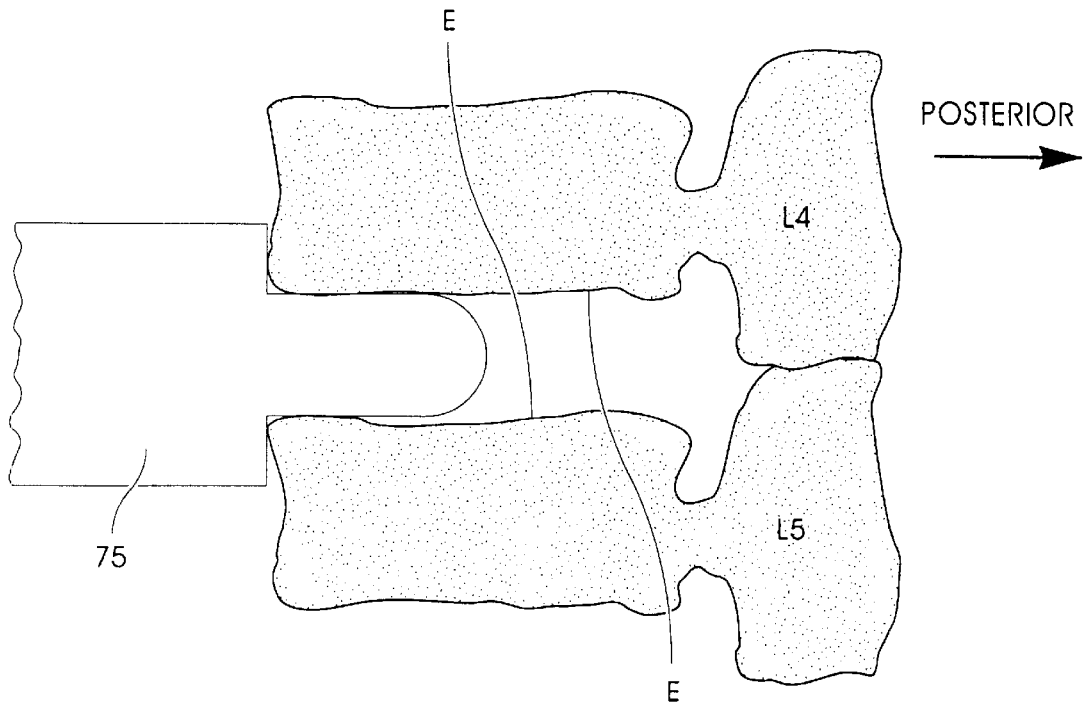
FIGS. 13(a)–13(d) show four steps of a method in accordance with one aspect of the invention for implanting the interbody fusion device, such as the device shown in FAG. 2.
Figure 13B:
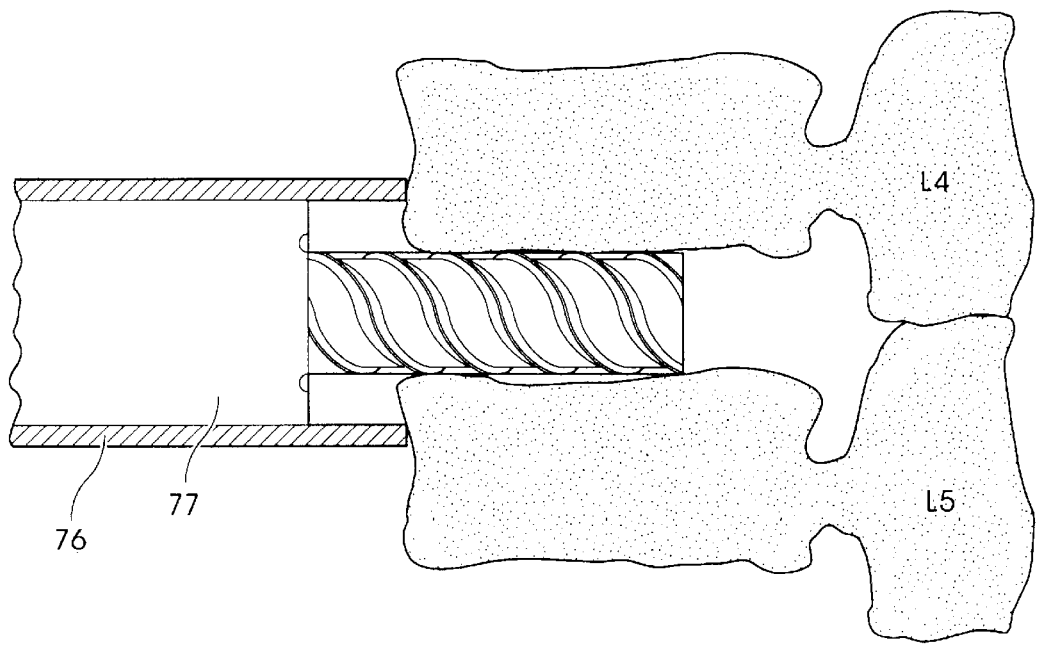
Figure 13C:
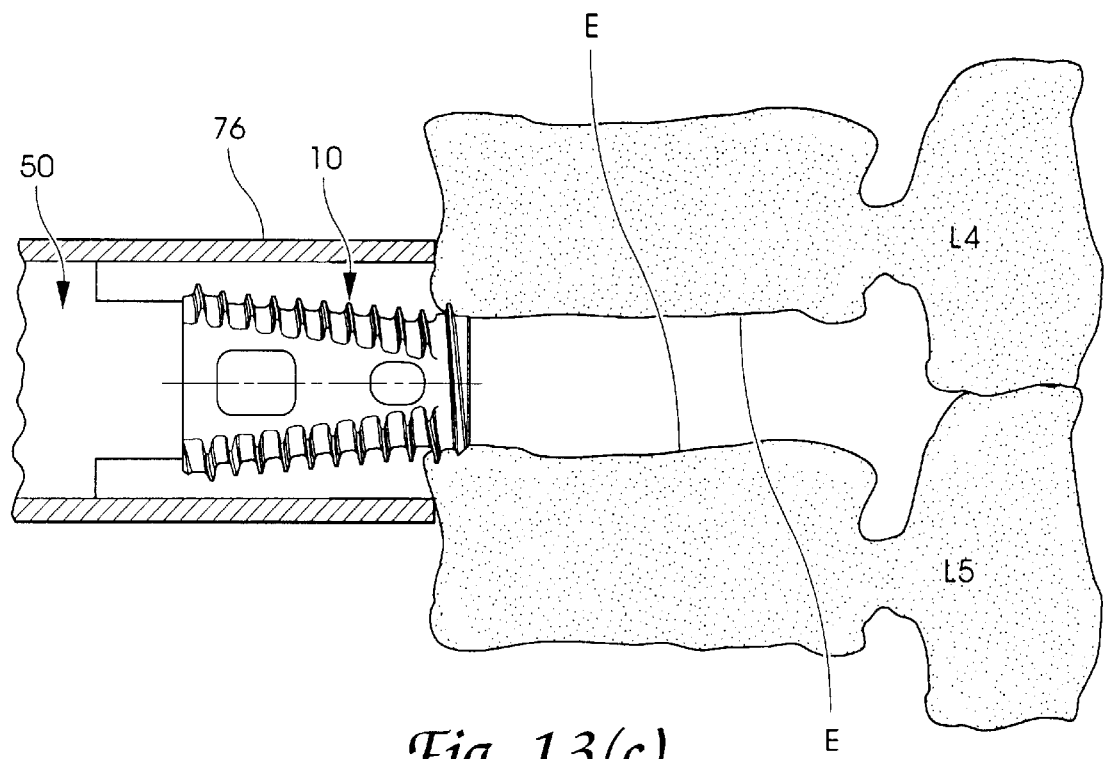
Figure 13D:
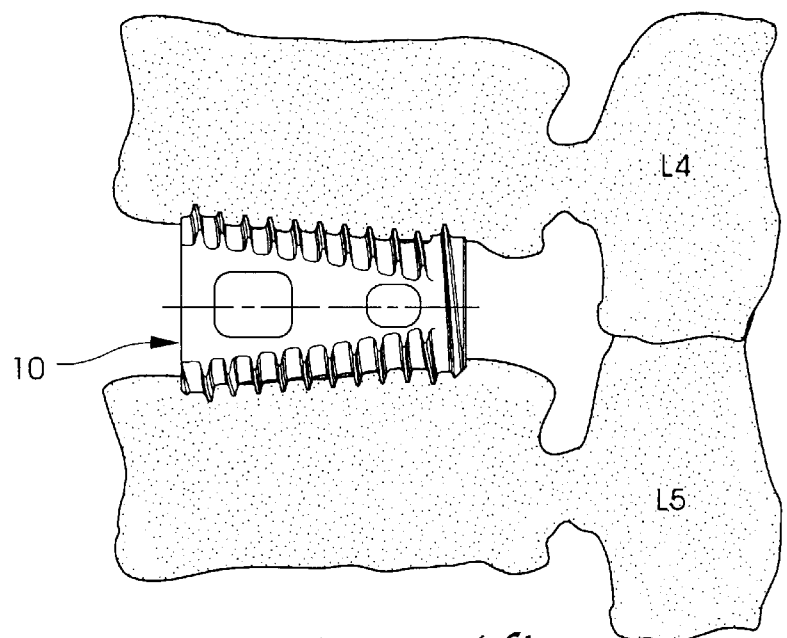
Figure 14A:
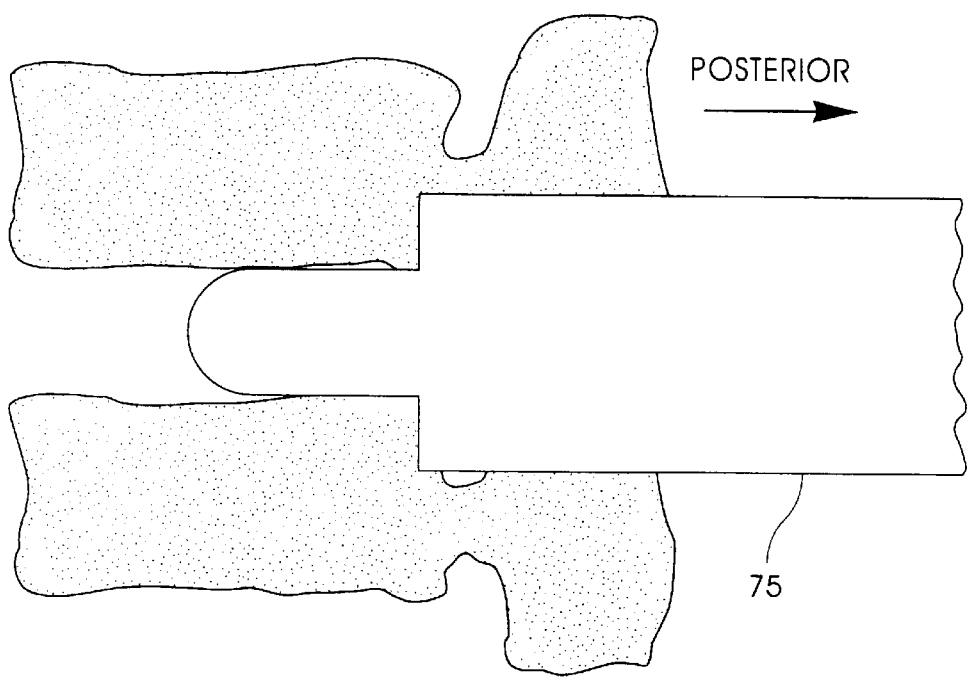
FIGS. 14(a)–14(d) depict steps of an alternative method for implanting the interbody fusion device, such as the device shown in FIG. 2.
Figure 14B:
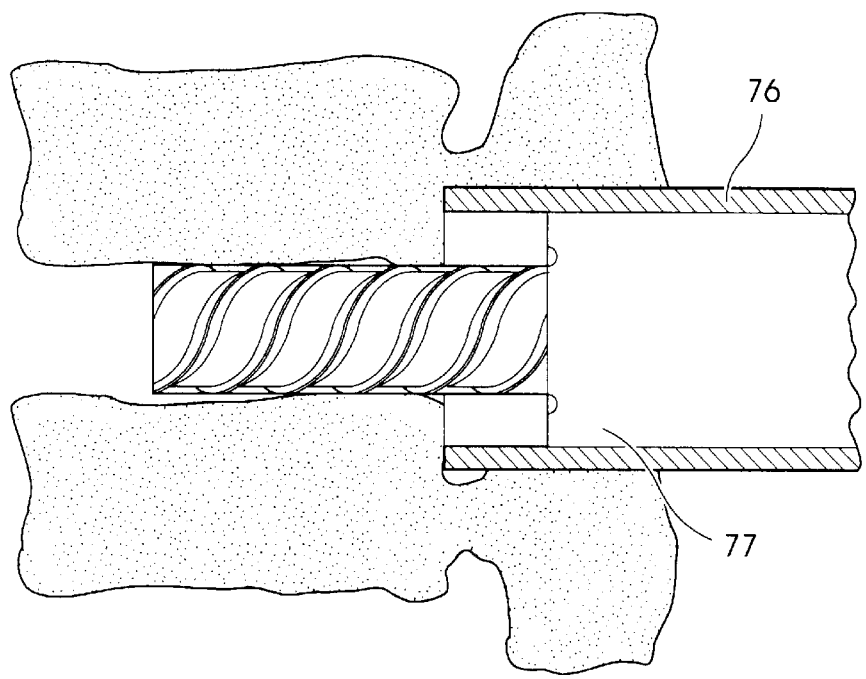
Figure 14C:
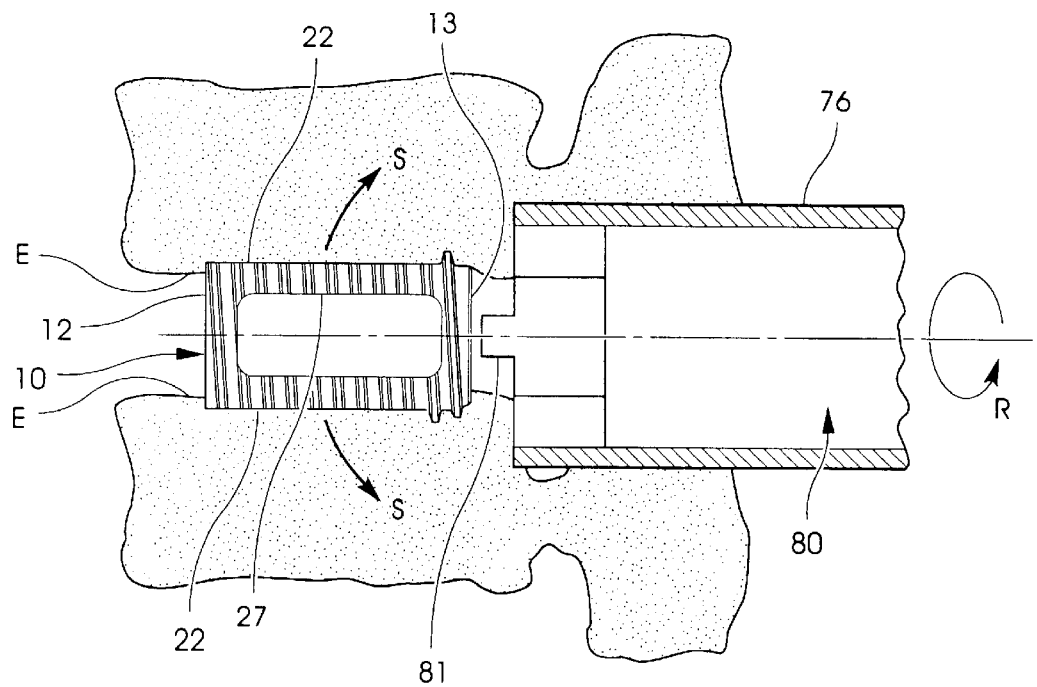
Figure 14D:
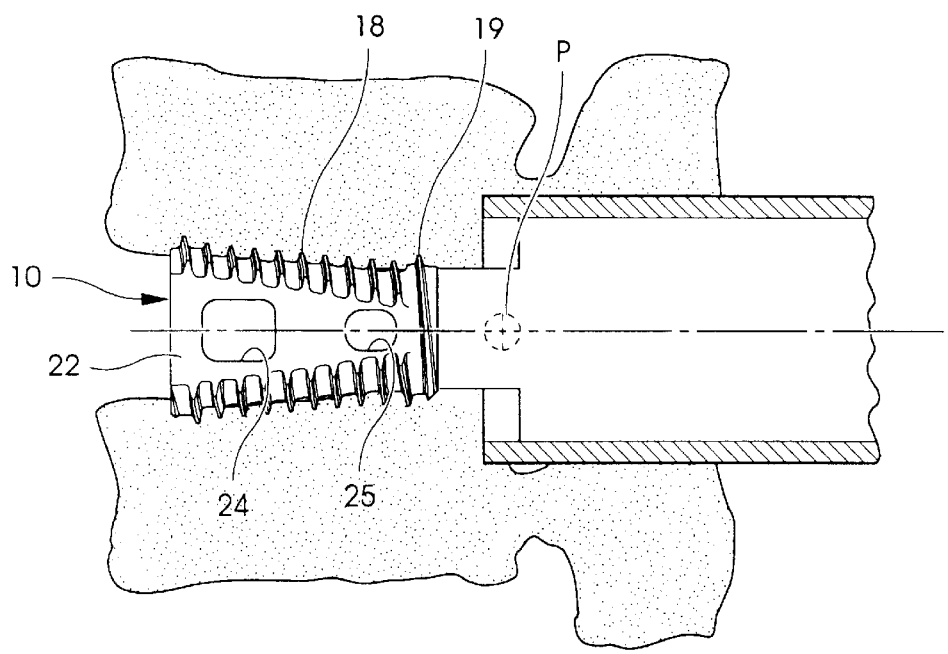

In a second inventive method, as depicted in FIGS. 13(a)–13(d), a posterior approach is implemented. The first two steps of the posterior approach are similar to that of the prior anterior approach, except that the dilator 75, outer sleeve 76 and drill 77 are introduced posteriorly into the instrumented region. This approach may require decortication and removal of vertebral bone to accept the outer sleeve 76. In the third step of this method, the fusion device 10 is inserted through the outer sleeve 76 into the dilated disc space. It is understood that the disc space is dilated only to the extent necessary to receive the implant with the truncated side walls 22 directly facing the vertebral end plates E. Thus, as shown in FIG. 13(c), the bone ingrowth slot 27 is facing laterally, rather than coronally, as expected for its final implanted position. A suitable driving tool 80 can be provided to project the fusion device 10 through the outer sleeve 76 and into the intra-discal space. In one embodiment, the driving tool 80 includes a projection 81 which is configured to engage a slot opening formed in the end wall 17 at the posterior end 13 of the fusion device 10. An internal thread (not shown) can be used to fix the device 10 to the driver 80.

Once the fusion device 10 has been advanced into the intra-discal space to the appropriate depth relative to the pivot axis P of the vertebrae, the driving tool 80 is used to rotate the implant in the direction of the rotational arrow R in FIG. 13(c). As the driving tool 80 is rotated, the device itself rotates so that the interrupted threads 18 start cutting into the vertebral bone at the end plates E. In this manner, the implant operates as a cam to separate the adjacent vertebrae in the direction of the spreading direction arrows S in FIG. 13(C). This camming approach provides a somewhat easier insertion procedure in that a single rotation is required to lock the implant into the vertebral bone. In contrast, the formerly discussed screw insertion technique requires continuous threading of the device into position.

With either technique, the position of the fusion device 10 with respect to the adjacent vertebrae can be verified by radiograph or other suitable techniques for establishing the angular relationship between the vertebrae. Alternatively, the preferred depth of insertion of the implant can be determined in advance and measured from outside the patient as the implant is positioned between the vertebrae.

It can be seen that the interbody fusion device 10, implant driver 50 and techniques of the present invention provide significant advantages over the prior devices and techniques. Specifically, the fusion device 10 provides a hollow threaded implant that maximizes the potential for bony fusion between adjacent vertebrae, while maintaining the integrity of the implant itself. It is understood that the spine endures significant loads along its axial length, which loads must be supported by the fusion device 10 at least until solid fusion is achieved. The device 10 also provides means for vascularization and tissue ingrowth to occur which speeds up the fusion rate and enhances the strength of the resulting fused bony mass. Another significant aspect is that the tapered shape of the implant allows the surgeon to restore and maintain the proper curvature or relative angle between vertebral bodies. This avoids the significant problems associated with prior devices in which product deformities arise and the spine goes out of balance. A further advantage achieved by the device and its implant driver is the capability for insertion either anteriorly or posteriorly using a laproscopic approach. Depending upon the vertebral level, either approach may be preferred, so it is important that the implant be adapted for insertion from either direction. Controlled insertion of the device is provided by the screw-in technique used for anterior insertion (vs. pounding in) and for the slide-in and cam method used for the posterior technique.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, while the device 10 has been disclosed for use in the spine, the structure and procedures of the present invention can also be used in other joint spaces, such as the ankle, wrist and subtalar joints. Moreover, while the device 10 of the preferred embodiment is shown tapered along its entire length, it is contemplated that a non-tapered or reverse tapered section can be added with the resulting device still falling within the scope of the invention.

What is claimed is:

1. A fusion device for facilitating arthrodesis in the disc space between adjacent vertebra, comprising:

an elongated body having a length between a first end and a second end thereof, and a first diameter at said first end sized to be greater than the space between the adjacent vertebrae;

said body having an outer surface with a pair of opposite cylindrical portions extending along substantially the entire length of said body and defining said first diameter, and a pair of substantially flat opposite side walls connected between said opposite cylindrical portions, said side walls extending along a substantial portion of said length of said body; and external threads defined on said pair of opposite cylindrical portions of said outer surface and extending along substantially the entire length of said body.

2. The fusion device of claim 1, wherein:

said flat side walls terminate near said first end; and said cylindrical portions and said threads are interrupted by said side walls and are circumferentially continuous thereafter from said side walls to said first end.

3. The fusion device of claim 2, wherein:

said body includes a second end opposite said first end; and said flat side walls terminate at said second end.

4. The fusion device of claim 3, wherein said opposite side walls each define a notch at said second end configured to receive a driving tool for implanting said device.

5. The fusion device according to claim 1, wherein said body is formed of a porous biocompatible material to permit bone tissue ingrowth into the device.

6. The fusion device according to claim 5 wherein said material is a composite comprising an open-celled substrate having interconnected porosity, said substrate infiltrated with a metal.

7. The fusion device according to claim 6 wherein said substrate is a carbonaceous material.

8. The fusion device according to claim 7 wherein said substrate is a carbon foam.

9. The fusion device according to claim 7 wherein said metal includes a group VB metal.

10. The fusion device according to claim 9, wherein said metal is tantalum.

11. A fusion device for facilitating arthrodesis in the disc space between adjacent vertebra, comprising:

an elongated body having a first end and a second end, an outer surface with cylindrical portions and a longitudinal axis, said implant body having threads on at least a portion of said cylindrical portions; and said outer surface defining at least two opposed bone ingrowth slots interrupting said threads, said bone ingrowth slots in substantial parallel alignment with said longitudinal axis.

12. The fusion device of claim 11, wherein said body defines a passage between said slots.

13. The fusion device of claim 12, wherein said passage is filled with bone growth inducing material.

14. The fusion device of claim 11, wherein said cylindrical portions are opposed and separated by substantially flat sidewalls.

15. The fusion device of claim 14, wherein said implant body defines a passage connecting said opposed bone ingrowth slots.

16. The fusion device of claim 11, wherein said two opposed slots are spaced from said first end and said second end.

17. The fusion device of claim 16, wherein said thread is continuous adjacent said first end and said second end.

18. The fusion device of claim 17, wherein said body defines a passage between said slots.

19. The fusion device of claim 18, wherein said passage is filled with bone growth inducing material.

20. A fusion device for facilitating arthrodesis in the disc space between adjacent vertebra comprising:

a generally cylindrical body including an outer surface having a diameter, a first end, a second end, and a longitudinal axis extending between said first end and said second end, said body having threads on a portion of the outer surface; and said outer surface defining at least two opposing slots in substantially parallel alignment with said longitudinal axis, said body defining a passage interconnecting said slots for allowing the growth of bone through the opposing slots, said passage having a width transverse to said longitudinal axis, said width substantially smaller than said diameter.

21. The fusion device of claim 20, wherein said threads are positioned on opposed sides of said outer surface.

22. The fusion device of claim 21, wherein said slots interrupt said threads.

23. The fusion device of claim 22, wherein said opposed sides are separated by substantially flat side walls.

24. A fusion device for facilitating arthrodesis in the disc space between adjacent vertebrae, comprising:

an elongated body having a length, a first end, a second end, and an external surface having cylindrical portions;

the body having external threads defined on the cylindrical portions of the external surface between the first and second ends; and the body including opposing slot openings providing a passageway through the body, the passageway allowing the growth of bone through the body between the slot openings.

25. The fusion device of claim 24, wherein said cylindrical portions are opposing and separated by two parallel side walls.

26. A fusion device for facilitating arthrodesis in the disc space between adjacent vertebrae, comprising:

an elongated body having a length and a first diameter at a first end sized to be greater than the space between the adjacent vertebrae;

said body having an outer surface with a pair of cylindrical portions and a pair of substantially flat opposite side walls between said opposite cylindrical portions, said side walls extending along a substantial portion of said length of said body;

external threads defined on said pair of opposite cylindrical portions of said outer surface and extending along substantially the entire length of said body; and said body defining at least one bone ingrowth slot in said cylindrical portion.

27. The fusion device of claim 26, wherein each of said cylindrical portions are adapted to contact one of the adjacent vertebrae.

* * * * *